United States Patent
List et al.

(10) Patent No.: US 10,682,417 B2
(45) Date of Patent: *Jun. 16, 2020

(54) TARGETED SENSITIZATION OF NON-DEL(5Q) MALIGNANT CELLS

(71) Applicant: H. LEE MOFFITT CANCER CENTER AND RESEARCH INSTITUTE, INC., Tampa, FL (US)

(72) Inventors: Alan List, Tampa, FL (US); Sheng Wei, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,483

(22) Filed: Apr. 3, 2018

(65) Prior Publication Data
US 2018/0369396 A1     Dec. 27, 2018

Related U.S. Application Data

(62) Division of application No. 14/761,641, filed as application No. PCT/US2014/012358 on Jan. 21, 2014, now Pat. No. 9,956,294.

(60) Provisional application No. 61/754,478, filed on Jan. 18, 2013.

(51) Int. Cl.
| | |
|---|---|
| A61K 31/713 | (2006.01) |
| A61K 31/711 | (2006.01) |
| A61K 38/00 | (2006.01) |
| A61K 31/454 | (2006.01) |
| C12N 15/113 | (2010.01) |
| A61K 45/06 | (2006.01) |
| A61K 47/54 | (2017.01) |

(52) U.S. Cl.
CPC .......... *A61K 47/54* (2017.08); *A61K 31/454* (2013.01); *A61K 31/711* (2013.01); *A61K 31/713* (2013.01); *A61K 38/00* (2013.01); *A61K 45/06* (2013.01); *A61K 47/549* (2017.08); *C12N 15/1137* (2013.01); *C12Y 301/03016* (2013.01); *C12Y 301/03048* (2013.01); *C12N 2310/14* (2013.01)

(58) Field of Classification Search
CPC combination set(s) only.
See application file for complete search history.

(56) References Cited

U.S. PATENT DOCUMENTS

| | | | |
|---|---|---|---|
| 5,034,506 A | 7/1991 | Summerton et al. | |
| 5,527,675 A | 6/1996 | Christensen et al. | |
| 5,539,082 A | 7/1996 | Nielsen et al. | |
| 5,623,049 A | 4/1997 | Loebberding et al. | |
| 5,714,331 A | 2/1998 | Buchardt et al. | |
| 5,736,336 A | 4/1998 | Buchardt et al. | |
| 5,773,571 A | 6/1998 | Nielsen et al. | |
| 5,786,571 A | 7/1998 | Bethel et al. | |
| 7,723,054 B2 | 5/2010 | Latz et al. | |
| 2010/0240542 A1 | 9/2010 | Soper et al. | |
| 2012/0128761 A1 | 5/2012 | Vagle et al. | |

FOREIGN PATENT DOCUMENTS

| | | |
|---|---|---|
| WO | 2016070014 A1 | 5/2016 |
| WO | 2016070045 A1 | 5/2016 |

OTHER PUBLICATIONS

Martin, et al. (2002) "Do Structurally Similar Molecules Have Similar Biological Activity?" Journal of Medicinal Chemistry, vol. 45(19): 4350-8. (Year: 2002).*
Barlow et al., "A p53-dependent mechanism underlies macrocytic anemia in a mouse model of human 5q-syndrome", Nat Med. 2010, 16(1):59-66.
Boultwood et al., "Narrowing and genomic annotation of the commonly deleted region of the 5q-syndrome", Blood. 2002, 99(12):4638-41.
Braasch, et al., "Locked nucleic acid (LNA): one-tuning the recognition of DNA and RNA", Chem Biol. 2001, 8(1):1-7.
Cheng et al., "Inhibition of dendritic cell differentiation and accumulation of myeloid-derived suppressor cells in cancer is regulated by S100A9 protein", J Exp Med. 2008, 205(10):2235-49.
Chiu et al., "siRNA function in RNAi: A chemical modification analysis", RNA 2003, 9:1034-1048.
Dutt et al. "Haploinsufficiency for ribosomal protein genes cause selective activation of p53 in human erythroid progenitor cells", Blood 2011, 117(9):2567-76.
Ebert et al., "Identification of RPS14 as a 5q-syndrome gene by RNA interference screen", Nature. 2008, 451(7176):335-9.

(Continued)

*Primary Examiner* — Jennifer Pitrak McDonald
(74) *Attorney, Agent, or Firm* — Thomas|Horstemeyer, LLP

(57) ABSTRACT

Disclosed are molecules for treating non-del(5q) MDS that mimic allelic deficiency in del5q MDS to sensitize the malignant clones of patient without del(5q). The disclosed molecule contains an inhibitor of Cdc25C, an inhibitor of PP2Acα, or a combination thereof, and a toll like receptor-9 (TLR9) targeting ligand. The molecule can also contain lenalidomide, or an analogue or derivative thereof. Also disclosed is a composition comprising the disclosed molecule in a pharmaceutically acceptable carrier. Also disclosed is a method for treating non-del(5q) meylodysplastic syndrome (MDS) in a subject by administering to the subject a therapeutically effective amount of the disclosed pharmaceutical composition.

12 Claims, 11 Drawing Sheets

Specification includes a Sequence Listing.

(56) References Cited

OTHER PUBLICATIONS

Ehrchen et al., "The endogenous Toll-like receptor 4 agonist S100A8/S100A9 (calprotectin) as innate amplifier of infection, autoimmunity, and cancer", J Leukoc Biol. 2009, 86(3):557-66.

Epling-Burnette et al., "Advancements in the molecular pathogenesis of myelodysplastic syndrome", Curr Opin Hematol. 2009, 16(2):70-6.

Estey, "Acute myeloid leukemia and myelodysplastic syndromes in older patients", J Clin Oncol. 2007, 25(14):1908-15.

Gabrilovich et al., "Myeloid-derived suppressor cells as regulators of the immune system", Nat Rev Immunol. 2009, 9(3):162-74.

Harborth et al. Sequence, Chemical, and Structural Variation of Small Interfering RNAs and Short Hairpin RNAs and the Effect on Mammalian Gene Silencing. Antisense and Nucleic Acid Development, 13, 83-105, 2003.

Kaelin, "The concept of synthetic lethality in the context of anticancer therapy", Nature reviews Cancer 2005, 5(9):689-98.

Kim et al., "Synthetic dsRNA Dicer substrates enhance RNAi potency and efficacy", Nat Biotechnol. 2005, 23(2):222-6.

Kim et al., "In situ vaccination against mycosis fungoides by intratumoral injection of a TLR9 agonist combined with radiation: a phase 1/2 study", Blood 2012, 119(2):355-63.

Klinman et al., "CpG motifs present in bacteria DNA rapidly induce lymphocytes to secrete interleukin 6, interleukin 12, and interferon gamma", Proc Natl Acad Sci U S A. 1996, 93(7):2879-83. PMCID: 39727.

Kortylewski et al., In vivo delivery of siRNA to immune cells by conjugation to a TLR9 agonist enhances antitumor immune responses. Nat Biotechnol. 2009, 27(10):925-32. PMCID: 2846721.

Krieg, "CpG still rocks! Update on an accidental drug", Nucleic Acid Ther. 2012, 22(2):77-89.

Krug et al., CpG-A oligonucleotides induce a monocyte-derived dendritic cell-like phenotype that preferentially activates CD8 T cells. J Immunol. 2003, 170(7):3468-77.

Kuninaka et al., "Expression of Toll-like receptor 9 in bone marrow cells of myelodysplastic syndromes is down-regulated during transformation to overt leukemia" Exp Mol Pathol. 2010, 88(2):293-8.

Lehmann et al., "Common deleted genes in the 5q-syndrome: thrombocytopenia and reduced erythroid colony formation in SPARC null mice", Leukemia. 2007, 21(9):1931-6.

List et al., "Opportunities for Trisenox (arsenic trioxide) in the treatment of myelodysplastic syndromes", Leukemia. 2003, 17(8):1499-507.

List et al., "Lenalidomide in the myelodysplastic syndrome with chromosome 5q deletion", N Engl J Med. 2006, 355(14):1456-65.

List et al., "Efficacy of lenalidomide in myelodysplastic syndromes", N Engl J Med. 2005, 352(6):549-57.

List et al., "Lenalidomide—A transforming therapeutic agent in myelodysplastic syndromes", Clin Lymphoma Myeloma 2009, 9(3):S302-4.

List et al., "Myelodysplastic syndromes", Hematology Am Soc Hematol Educ Program 2004, 297-317.

Liu et al., "The p53-Mdm2 network in progenitor cell expansion during mouse postnatal development", J Pathol. 2007, 213(4):360-8.

Mcdermott et al., "Comparison of human cord blood engraftment between immunocompromised mouse strains", Blood 2010, 116(2):193-200.

Padmapriya et al., "Synthesis of Oligodeoxynucleoside Methylphosphonothioates", Bioorg. & Med. Chem. Lett. 1993, 3(4):761-764.

Reinhardt et al., Exploiting synthetic lethal interactions for targeted cancer therapy, Cell Cycle 2009, 8(19):3112-9. PMCID: 3057180.

Rose et al., "Functional polarity is introduced by Dicer processing of short substrate RNAs", Nucleic Acids Res. 2005, 33(13):4140-56. PMCID: 1180746.

Stirchak et al., "Uncharged stereoregular nucleic acid analogs. 1. Synthesis of a cytosine-containing oligomer with carbamate internucleoside linkages", Organic Chem. 1987, 52:4202-4206.

Tehranchi et al., Persistent malignant stem cells in del(5q) myelodysplasia in remission. N Engl J Med. 2010, 363(11):1025-37.

Uccellini et al., "Autoreactive B cells discriminate CpG-rich and CpG-poor DNA and this response is modulated by IFN-alpha", J Immunol. 2008, 181(9):5875-84. PMCID: 2584609.

Uhlmann et al., "Antisense Oligonucleotides: A New Therapeutic Principle", Chemical Reviews 1990, 4:545-561.

Unger et al., "Lentiviral-Mediated HoxB4 Expression in Human Embryonic Stem Cells Initiates Early Hematopoiesis in a Dose-Dependent Manner but Does Not Promote Myeloid Differentiation", Stem Cells 2008, 26:2455-2466.

Wei et al., "Lenalidomide promotes p53 degradation by inhibiting MDM2 auto-ubiquitination in myelodysplastic syndrome with chromosome 5q deletion", Oncogene 2013, 32:1110-1120.

Wei et al., "A critical role for phosphatase haplodeficiency in the selective suppression of deletion 5q MDS by lenalidomide", Proc Natl Acad Sci U S A. 2009, 106(31):12974-9.

Wei et al., "Microenvironment Induced Myelodysplastic Syndrome (MDS) in S100A9 Transgenic Mice Caused by Myeloid-Derived Suppressor Cells (MDSC)", ASH Annual Meeting Abstracts.

Xin et al., "Systemic treatment with CpG-B after sublethal rickettsial infection induces mouse death through indoleamine 2,3-dioxygenase (IDO)", PLoS ONE 2012, 7(3):e34062. PMCID: 3314704.

International Search Report and Written Opinion, issued in International Application No. PCT/US14/12358 dated Apr. 23, 2014.

\* cited by examiner

Healthy

MDS del 5q
Ribosomal stress

TARGETED SENSITIZATION OF NON-DEL(5Q) MALIGNANT CELLS

CROSS-REFERENCE TO RELATED APPLICATIONS

This application claims benefit of U.S. Utility application Ser. No. 14/761,641, filed Jul. 17, 2015, which is a national stage application filed under 35 U.S.C. § 371 of PCT Application No. PCT/US2014/012358, filed Jan. 21, 2014, which claims benefit of U.S. Provisional Application No. 61/754,478, filed Jan. 18, 2013, each of which is hereby incorporated herein by reference in their entirety.

TECHNICAL FIELD

This application relates generally to compositions and methods for treating myelodysplastic syndromes (MDS).

BACKGROUND

Myelodysplastic syndromes (MDS) are hematopoietic stem cell malignancies with a rising prevalence owing to the aging of the American population. MDS comprise a group of malignant hematologic disorders associated with impaired erythropoiesis, dysregulated myeloid differentiation and increased risk for acute myeloid leukemia (AML) transformation. The incidence of MDS is increasing with 15,000 to 20,000 new cases each year in the United States and large numbers of patients requiring chronic blood transfusions. Ineffective erythropoiesis remains the principal therapeutic challenge for patients with more indolent subtypes, driven by a complex interplay between genetic abnormalities intrinsic to the MDS clone and senescence dependent inflammatory signals within the bone marrow (BM) microenvironment. Although three agents are approved for the treatment of MDS in the United States (US), lenalidomide (LEN) represents the only targeted therapeutic. Treatment with LEN yields sustained red blood cell transfusion independence accompanied by partial or complete resolution of cytogenetic abnormalities in the majority of patients with a chromosome 5q deletion (del5q), whereas only a minority of patients with non-del5q MDS achieve a meaningful response, infrequently accompanied by cytogenetic improvement. Although responses in patients with del5q MDS are relatively durable, lasting a median of 2.5 years, resistance emerges over time with resumption of transfusion dependence.

The available effective treatment options for patients with non-del(5q) is limited. Notably, MDS cases grow year over year due the increase in the American aging population and its combination. Frequently they are misdiagnosed leading to failure to treat serious infections or the wasting of expensive treatment and precious resources. Once a proper diagnosis is made patients have to rely on frequent blood transfusion and non-specific chemotherapy which have severe side effects and have limited benefit for patients with non-del(5q). The lack of effective treatment on MDS patients without del(5q) contributes to the enormous burden of this disease on both patient and caregivers and increases the risk of AML transformation. Therefore, there is definitely a need to develop a specific targeted therapeutic in this patient population.

SUMMARY

Disclosed are molecules for treating non-del(5q) meylodysplastic syndrome (MDS) that mimic allelic deficiency in del5q MDS to sensitize the malignant clones of patient without del(5q). The disclosed molecule contains a Cdc25C inhibitor, a PP2Acα inhibitor, or a combination thereof, and a toll like receptor-9 (TLR9) targeting ligand. In some embodiments, the inhibitors are functional nucleic acids, such as siRNA. In some embodiments, the inhibitors are phosphatase inhibitors. The molecule can further contain lenalidomide, or an analogue or derivative thereof.

Also disclosed is a pharmeutical composition comprising the disclosed molecule in a pharmaceutically acceptable carrier. Also disclosed is a method for treating non-del(5q) MDS in a subject by administering to the subject a therapeutically effective amount of the disclosed pharmaceutical composition.

Also disclosed are methods treating non-del(5q) MDS in a subject that involve administering a composition to the subject that is targeted to TLR9 positive cells and inhibits Cdc25C, PP2Acα, or a combination thereof. The method can further involve administering to the subject lenalidomide, or an analogue or derivative thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows a Cdc25C siRNA (SEQ ID NO: 1) linked to siPP2A siRNA (SEQ ID NO:2) by a C3 carbon linker, which is conjugated with lenalidomide (LPN) by a C10 linker. FIG. 1B shows linked siPP2A linked to Cdc25C by C3 carbon linker without coupling with LEN, which is used as control. FIG. 1C shows complete structure of CpG-si-LEN, where CpG is coupled with siPP2A-Cdc25C and LEN in a single molecule as indicated.

FIGS. 2A-2B are images of an RT-PCR gel (FIG. 2A) and Western blot (FIG. 2B) to detect PP2A and Cdc25C gene (FIG. 2A) and protein (FIG. 2B) expression in U937 cells infected with mock (lane 1), lentiviral vectors encoding non-target shRNA control (lane 2), shCdc25C (lane 3), shPP2Acα (lane 4), shCdc25C and PP2Acα (lane 5) and negative for PCR (lane 6) and harvested 48 hours after incubation. FIGS. 2C and 2D are bar graphs showing P2Acα and Cdc25c mRNA expression (copies/GAPDH) in U937 cells infected with mock, lentiviral vectors encoding non-target shRNA control, shCdc25C, shPP2Acα, or shCdc25C and PP2Acα. FIGS. 2E-2F are bar graphs showing apoptosis (%) in U937 cells (E) or BM-MNC (F) that were infected with lentiviral vectors containing various constructs as indicated for 48 hours and then treated with or without lenalidomide at the concentration of 5 nM for additional 48 hours before being analyzed for apoptosis. FIG. 2G(i)-2G(iv) are graphs showing cell cycle analysis of BM-MNC from MDS patients with a normal karyotype after Cdc25C/PP2Acα double-knockdown plus lenalidomide treatment. A representative result is shown from one patient. A total of five different MDS patients were tested.

FIGS. 3A-3B show PP2Acα and Cdc25C gene (FIG. 3A) and protein (FIG. 3B) expression in U937 cells 48 hours after siPP2A and Cdc25c linked by C3 linker were administered. FIG. 3C is a bar graph showing gene silencing by linked siRNA is sustained at day 6 by Q-PCR after administration. FIG. 3D is a bar graphs showing apoptosis (% 7AAD) 72 hours after linked siPP2A and Cdc25c coupled with LEN were administered to U937 cells.

FIG. 4A shows flow cytometric analysis of TLR9 surface expression on BM-MNCs from MDS patients or age-matched healthy donors with anti-TLR9. FIG. 4B shows flow cytometric analysis of TLR9 surface expression on CD34+CD90+ double positive HSCs from MDS patients or age-matched healthy donors with anti-TLR9. One representative experiment is shown and a total of 6 patients and 4 controls were examined and summarized in FIG. 4C.

FIG. 5B is a graph showing increased intracellular FITC positive hone marrow cells examined by intracellular flow cytometric analysis after injection of FITC labeled CpG conjugates (25 µg/100 µl/per mouse) at 24 or 48 hours by tail injection.

FIG. 6A is a diagram showing that in normal individual ribosomal stress induced p53 expression which causes abnormal cells to undergo apoptosis/G1 arrest and induce the negative regulator MDM2. FIG. 6B is a diagram showing that in del5q MDS there is an increase in RPS binding to MDM2 and haplo-deficiency of PP2A/CDC25c leading to MDM2 auto-ubiquitination that causes p53 accumulation. Subsequently, it causes HSC/HPC damage leading to the development of anemia. FIG. 6C is a diagram showing that synthetic lethal agent LEN (LEN) can rescue HSC/HPC by targeting PP2A/CDC25 and stabilizing MDM2 promoting p53 degradation. FIG. 6D is a diagram showing that in order to allow LEN to target non5q MDS cells, future therapies should target PP2A/Cdc25C expression to mimic the del5q MDS by siRNA or phosphatase inhibitors in combination with LEN.

DETAILED DESCRIPTION

Figure 1:
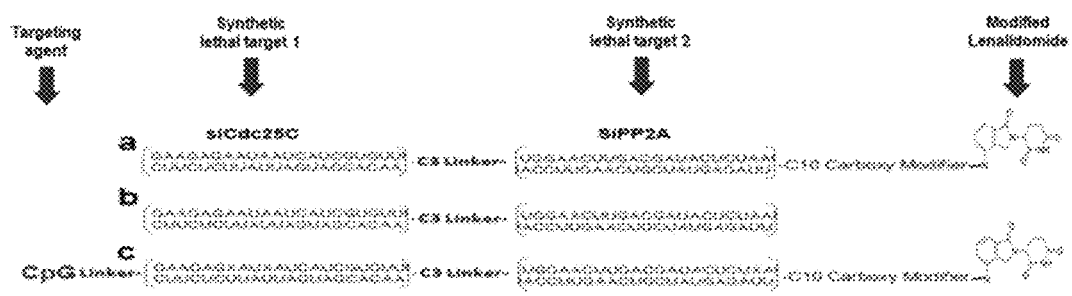
FIG. 1 is a depiction of CpG-si-LEN conjugates.

Lenalidomide (LEN) selectively suppresses del5q clones by exploiting the process of synthetic lethality. LEN inhibits two haplodeficient phosphatases encoded within or near the proximal commonly deleted region (CDR) at 5q31, i.e., PP2Acα and Cdc25C, key regulators of the G2/M checkpoint, resulting in sustained arrest of del5q progenitors. Allelic deletion of the ribosomal protein (RP) RP-S14 gene encoded within the distal CDR disrupts ribosome assembly, leading to release of free RPs that bind to MDM2, triggering its degradation with consequent p53 activation in affected erythroid progenitors. A murine model of the human 5q-syndrome generated by allelic deletion of the syntenic genes within the human 5q32-33 CDR showed that p53 inactivation rescues the hematologic phenotype, indicating that the molecular pathogenesis of del5q MDS is p53-dependent. Interestingly, BM specimens from del(5q)MDS patients resistant to LEN over-expressed PP2Acα accompanied by restored p53 accumulation in erythroid precursors, findings consistent with in vitro studies showing that forced PP2Acα overexpression promotes LEN resistance. The precise mechanism of LEN's selectivity towards patients with del (5q) was identified. However, these patients only account for 5-10 percent of MDS casts while the majority of non-del(5q) patients are not responsive to LEN.

Knockdown of PP2Acα and Cdc25C gene expression by siRNA in non-del5q cells sensitizes them to LEN through mimicry of del5q allelic deficiency. Moreover, MDS progenitors, and in particular MDS stem cells (HSC), overexpress Toll-like receptor (TLR)-9, permitting development of a specific drug delivery and targeting approach using unmethylated CpG oligonucleotides (natural ligands for TLR9) linked to bioactive payloads for cellular delivery.

Synthetic lethality is a concept that exploits the vulnerability of cancer cells which have lost one mechanism of DNA repair by blocking a second/rescue pathway with a drug or inhibitor, so that cell have effectively lost two DNA repair pathway and failed to repair DNA damage, leading to cell death. This concept is particularly applicable to MDS with del(5q). In this case, treatment with LEN yields sustained therapeutic effect in the majority of patients with del5q. However, the unique del5q MDS pathological mechanisms and LEN selectively suppresses del5q clones by exploiting the process of synthetic lethality has suggested a novel pathway (FIG. 6). Deletion of RPS14, a component of the 40S ribosomal subunit, is a key determinant of ineffective erythropoiesis in del5q. In a mouse model of the human 5q-syndrome with haploinsufficiency of RPS14, inactivation of p53 rescued the hematologic phenotype confirming the critical role of p53 in the del5q MDS phenotype. Disruption of ribosome assembly as a result of deletion or mutation of genes encoding ribosomal proteins (RP) leads to nucleolar stress and sequestration of the human homologue of the E3 ubiquitin ligase MDM2 by free RP, triggering its autologous degradation and consequent p53 stabilization. MDM2$^{-/-}$ null mice with homozygous wild type TP53 develop a progressive cytopenia arising from reduced proliferative potential of hematopoietic progenitors. Introduction of a single copy of MDM2 is sufficient to rescue the hematopoietic defect. Analysis of primary del5q MDS specimens confirmed that p53 is over-expressed in a lineage-restricted manner. Treatment with LEN restores MDM2 stability to promote p53 degradation in both a cell line model and primary del(5q) MDS specimens, an effect that is accompanied by suppression of downstream p53 effector genes. LEN may disrupt RPLs, such as RPS14 association with MDM2, and stabilize MDM2-mediated proteasomal degradation of p53 in del5q progenitors together. This suggests that modulation of the RP-p53-MDM2 cascade may represent an alternative strategy to restore erythropoiesis in del5q MDS without suppressing the clone.

Figure 6A:
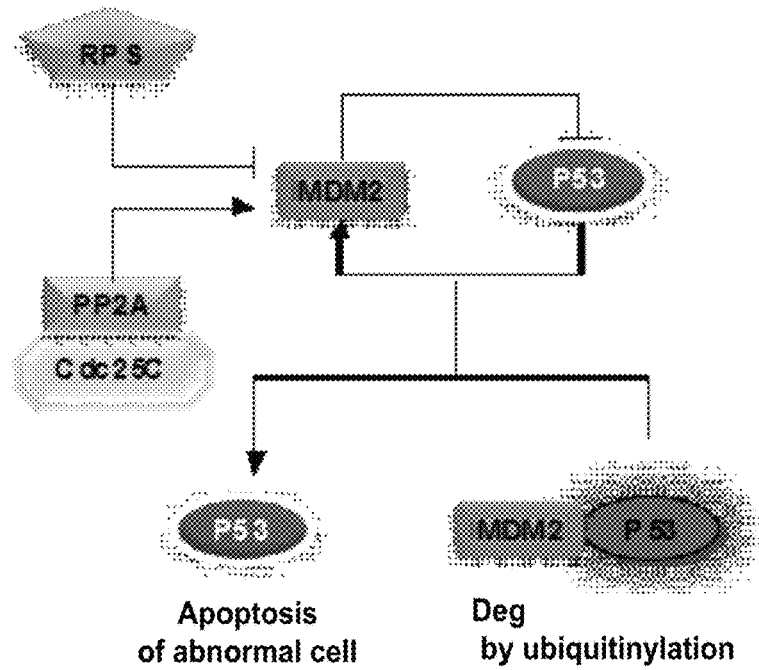
FIG. 6A-D shows MDS disease mechanism and perspective of potential application of synthetic lethality.
Figure 6B:
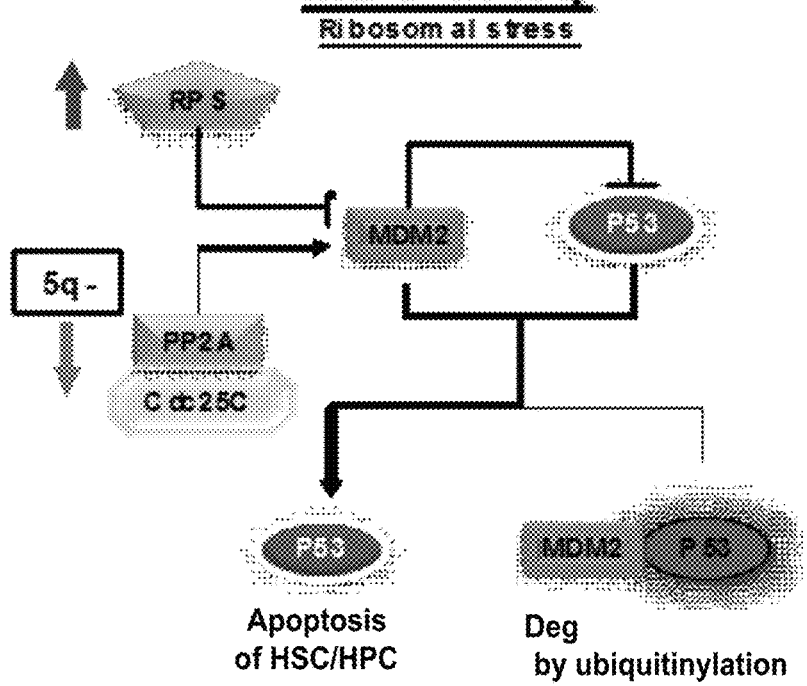
Figure 6C:
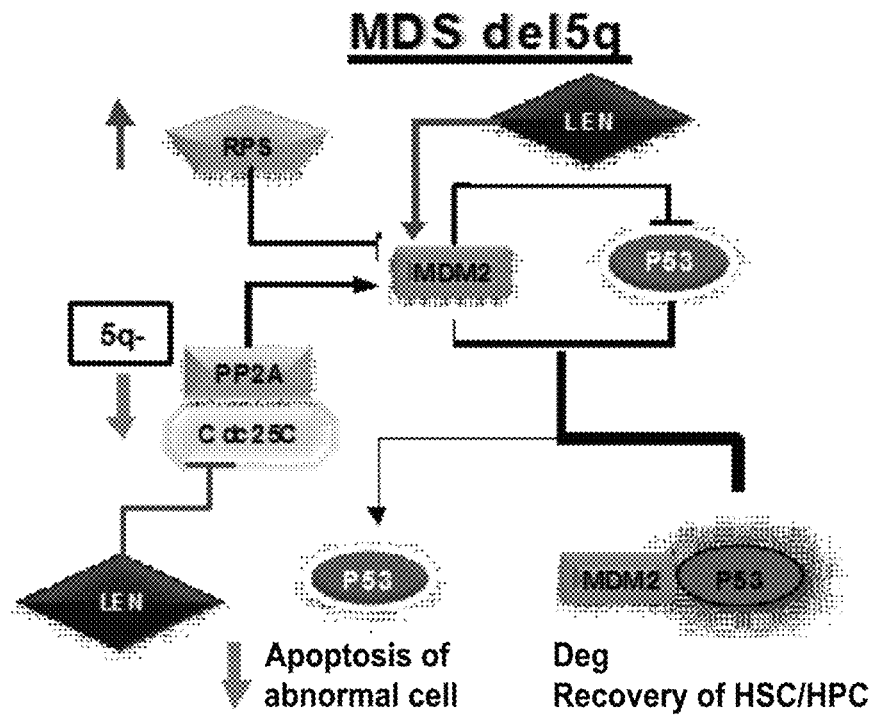
Figure 6D:
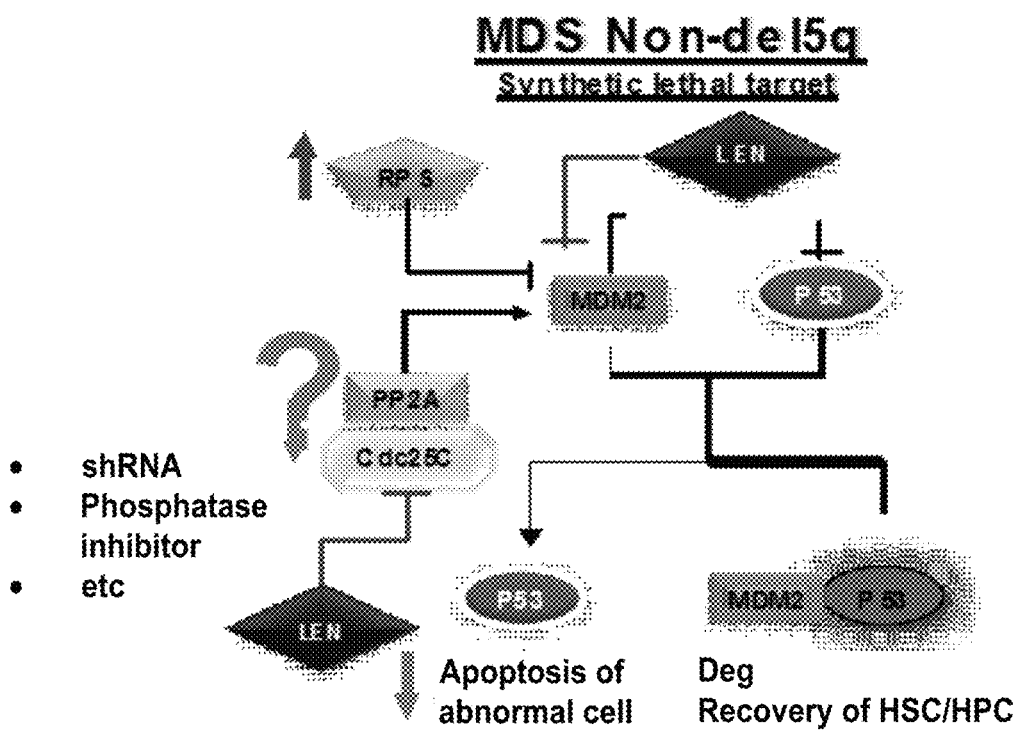

As mentioned above, patients with del5q have the increased sensitivity to LEN suggesting that allelic deletion of a gene(s) within this chromosomal segment, may serve as a molecular drug target for LEN. Notably, knockdown of PP2Acα and Cdc25C gene expression by siRNA in non-del5q cells sensitizes them to LEN through mimicry of del5q allelic deficiency; thereby supporting the notion that applied synthetic lethality may be transferable to non-del5q MDS (FIG. 6D). Therefore, targeting malignant cells through a combination that affects those pathway components can provide a powerful therapy for non del5q malignancies.

Therapeutic development for MDS has relied upon empiricism owing to the limited understanding of fundamental patho-genetic disease mechanisms. Inhibiting the haplo-deficient Cdc25C and PP2Acα LEN can act on non-del(5q) clones and lead to cell G2 arrest and apoptosis, thereby rescuing hematopoiesis. These findings provide a strong rationale to develop clinical strategies to extend this approach to MDS patients without del(5q). Importantly, non-del(5q) clones express very high levels of Toll like receptor 9 (TLR-9), which can be targeted through its natural ligand CpG. Based on studies that reduced gene dosage of Cdc25C and PP2A are responsible for LEN responsiveness in del(5q), this concept of applied synthetic lethality can be extended to non-del5q MDS by disease selective, targeted suppression of PP2Acα and Cdc25C using CpG-siRNA-LEN conjugates.

The disclosed strategy builds upon findings that primary human MDS progenitors and HSC express high levels of TLR-9 that bind to CpG and internalize LEN-siRNA specific to Cdc25C and PP2A conjugates to mimic allelic deficiency in del5q MDS to sensitize the malignant clones of patient without del(5q).

In addition, many other cancers, including lung and breast, also have high TLR-9 expression, may also be therapeutically targeted with the disclosed applied synthetic lethality by replacing of Lenalidomide with a suitable cytotoxic drug for that cancer.

Targeted Molecules that Mimic Allelic Deficiency in del5q MDS

Therefore, molecules are disclosed for treating non-del (5q) MDS that mimic allelic deficiency in del5q MDS to sensitize the malignant clones of patient without del(5q). The disclosed molecule contains an inhibitor of Cdc25C, an inhibitor of PP2Acα, or a combination thereof. The molecule further contains a toll like receptor-9 (TLR9) targeting ligand to effectively target the Cdc25C/PP2Acα inhibitors to MDS stem cells (HSC). The molecule can further contain lenalidomide ((RS)-3-(4-Amino-1-oxo 1,3-dihydro-2H-isoindol-2-yl)piperidine-2,6-dione), or an analogue or derivative thereof. Alternatively, the molecule can be administered in combination with lenalidomide, or an analogue or derivative thereof.

For example, in some embodiments, the molecule is defined by a formula selected from the group consisting of:

TTL--IC--LEN,

TTL--IP--LEN,

TTL--IC,

TTL--IP,

TTL--IC--IP,

TTL--IP--IC,

TTL--IC--IP--LEN, or

TTL--IP--IC--LEN, wherein "TTL" represents a TLR9 targeting ligand,
wherein "IC" represents an inhibitor of Cdc25C,
wherein "IP" represents an inhibitor of PP2Acα,
wherein "LEN" represents an lenalidomide, or an analogue or derivative thereof, and
wherein "--" represents a bivalent linker.

TLR9 Targeting Ligand

The TLR9 targeting ligand ("TTL") can be a CpG oligodeoxynucleotide, such as an unmethylated CpG oligodeoxynucleotide, or an analogue or derivative thereof that binds TLR9. CpG oligodeoxynucleotides (or CpG ODN) are short single-stranded synthetic DNA molecules that contain a cytosine triphosphate deoxynucleotide followed by a guanine triphosphate deoxynucleotide. The "p" refers to the phosphodiester link between consecutive nucleotides, although some ODN have a modified phosphorothioate (PS) backbone instead. When these CpG motifs are unmethylated, they act as immunostimulants. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is constitutively expressed only in B cells and plasmacytoid dendritic cells (pDCs) in humans and other higher primates. Moreover, MDS progenitors, and in particular MDS stem cells (HSC), overexpress Toll-like receptor (TLR)-9, permitting development of a targeting approach using unmethylated CpG oligonucleotides linked to bioactive payloads for cellular delivery.

Synthetic CpG ODN differ from microbial DNA in that they have a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake. The poly G tails form intermolecular tetrads that result in high molecular weight aggregates. Numerous sequences have been shown to stimulate TLR9 with variations in the number and location of CpG dimers, as well as the precise base sequences flanking the CpG dimers. This led to the creation of five unofficial classes or categories of CpG ODN based on their sequence, secondary structures, and effect on human peripheral blood mononuclear cells (PBMCs). The five classes are Class A (Type D), Class B (Type K), Class C, Class P, and Class S.

Bivalent Linker

The bivalent linker can be any molecule suitable to link a compound or nucleic acid to a polynucleotide sequence. Methods and compositions for conjugating biomolecules, such as polynucleotides, are disclosed in G. T. Hermann, Bioconjugate Techniques (2$^{nd}$ ed.), Academic Press (2008), which is incorporated by reference in its entirety for the teaching of these techniques.

In some embodiments, the bivalent linker is a non-nucleotidic linker. As used herein, the term "non-nucieotidic" refers to a linker that does not include nucleotides or nucleotide analogs. Typically, non-nucleotidic linkers comprise an atom such as oxygen or sulfur, a unit such as C(O), C(O)NH, SO, SO$_2$, SO$_2$NH, or a chain of atoms, such as substituted or unsubstituted alkyl, substituted or unsubstituted alicenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylallcyl, alkylheterocyclylalkenyl, alkylhererocyclylalkynyl, alkenylheterocyclylalkyl, alkenylheterocyclylalkenyl, alkenylheterocyclylalkynyl, alkynytheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, SS, S(O), SO2, N(R$^1$)$_2$, NR$^1$, C(O), C(O)O, C(O)NH, —OPO$_2$O—, cleavable linking group, substituted or unsubstituted aryl, substituted or unsubstituted heteroaryl, substituted or unsubstituted heterocyclic; where R' is hydrogen, acyl, aliphatic or substituted aliphatic.

In some embodiments, the bivalent linker comprises at least one cleavable linking group, i.e. the linker is a cleavable linker. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the linked components after transport to the desired target. The intended nature of the conjugation or coupling interaction, or the desired biological effect, will determine the choice of linker group. For example, the bivalent linker can comprise a photocleavable PC linker. In some embodiments, the oligonucleotide is cleavable by dicer to produce isolate individual siRNA from the oligonucleotide.

Additional examples of linkers include Hexanediol, Spacer 9, Spacer 18, 1',2'-Dideoxyribose (dSc), and I-Linker.

Cdc25C or PP2Acα Inhibitors

The disclosed Cdc25C and/or PP2Acα inhibitors can be any agent that is effective to inhibit one or more activities of Cdc25C and/or PP2Acα. "Activities" of a protein include, for example, transcription, translation, intracellular translocation, secretion, phosphorylation by kinases, cleavage by proteases, homophilic and heterophilic binding to other proteins, ubiquitination. These proteins are phosphatases. Therefore, the inhibitor can also inhibit the phosphatase activity of Cdc25C and/or PP2Acα. The inhibitor, can alternatively inhibit gene expression (transcription and/or translation) of Cdc25C and/or PP2Acα.

In some embodiments, the disclosed Cdc25C or PP2Acα inhibitor are functional nucleic acids. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, or RNA interference (RNAi) molecules.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are oligonucleic acid or peptide molecules that bind to a specific target molecule. Typically aptamers are small nucleic acids ranging from 15-50 bases in length that fold into defined secondary and tertiary structures, such as stem-loops or G-quartets. Aptamers can bind small molecules as well as large molecules. Aptamers can bind very tightly with $K_d$'s from the target molecule of less than $10^{-12}$M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNasc P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate.

Gene expression can also be effectively silenced in a highly specific manner through RNA interference (RNAi). This silencing was originally observed with the addition of double stranded RNA (dsRNA). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends. In an ATP dependent step, the siRNAs become integrated into a multi-subunit protein complex, commonly known as the RNAi induced silencing complex (RISC), which guides the siRNAs to the target RNA to sequence. At some point the siRNA duplex unwinds, and it appears that the antisense strand remains bound to RISC and directs degradation of the complementary mRNA sequence by a combination of endo and exonucleases. However, the effect of RNAi or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for Cdc25C and PP2Acα.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

In some embodiments, the functional nucleic acid inhibitor of Cdc25C is an siRNA. For example, the Cdc25C siRNA can have the nucleic acid sequence 5'-GAAGA-GAAUAAUCAUCGUGUU-3' (SEQ ID NO:1), or a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:1. Similarly, the functional nucleic acid inhibitor of PP2Acα can also be an siRNA. For example, the PP2Acα siRNA can have the nucleic acid sequence 5'-UGGAAC-UUGACGAUACUCUAA-3' (SEQ ID NO:2), or a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to SEQ ID NO:2.

Oligonucleotide Modifications

The disclosed molecules containing oligonucleotides can be modified to improve activity and/or stability. Compositions and methods for increasing stability of nucleic acid half-life and nuclease resistance are known in the art, and can include one or more modifications or substitutions to the nucleobases, sugars, or linkages of the polynucleotide. For example, the polynucleotide can be custom synthesized to contain properties that are tailored to fit a desired use. Common modifications include, but are not limited to use of locked nucleic acids, unlocked nucleic acids (UNA's), morpholinos, peptide nucleic acids (PNA), phosphorothioate linkages, phosphonoacetate, linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiment, the polynucleotide includes intemucleotide linkage modifications such as phosphate analogs having achiral and uncharged intersubunit linkages, or uncharged morpholino-based polymers having achiral intersubunit linkages. Some intemucicotide linkage analogs include morpholidate, acetal, and polyamide-linked heterocycles. Locked nucleic acids (LNA) are modified RNA nucleotides. Commercial nucleic acid synthesizers and standard phosphoramidite chemistry are used to make LNAs. Other backbone and linkage modifications include, but are not limited to, phosphorothioates, peptide nucleic acids, tricycle-DNA, decoy oligonucleotide, ribozymes, spiegelm.ers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuratn disulfide (TETD) or 3H-1, 2-bensodithiol-3-one 1, 1-dioxide (BDTD).4 The latter methods avoid the problem of elemental sulfur's insolubility in most organic solvents and the toxicity of carbon disulfide. The TETD and BDTD methods also yield higher purity phosphorothioates.

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like.

In some embodiments, the polynucleotide includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro. Moreover, one report recently suggested 2'-F modified siRNAs have enhanced activity in cell culture as compared to 2'-OH containing siRNAs. 2'-F modified siRNAs are functional in mice but that they do not necessarily have enhanced intracellular activity over 2'-OH siRNAs.

In some embodiments the polynucleotide include one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE) 2'-O, 4'-C-methylene (LNA), 2'-O-(methoxyethyl) (2'-OME) and 2'-O-(N-(methyl)acetamido) (2'-OMA).

Pharmaceutical Composition

Also disclosed is a pharmaceutical composition comprising the disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. P P. Gerbino, Lippincott Williams & Wilkins, Philadelphia, Pa. 2005. Typically, apt appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium to chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amities and substituted ethanolamines.

Methods of Treatment

Also disclosed is a method for treating non-del(5q) meylodysplastic syndrome (MDS) in a subject by administering to the subject a therapeutically effective amount of the disclosed pharmaceutical composition. Also disclosed are methods treating non-del(5q) MDS in a subject that involve administering a composition to the subject that is targeted to TLR9 positive cells and inhibits Cdc25C, PP2Acα, or a combination thereof. The method can further involve administering to the subject lenalidomide, or an analogue or derivative thereof.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by to injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for MDS. Thus, the method can further comprise identifying a subject at risk for MDS prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule containing lenalidomide is administered in a dose equivalent to parenteral administration of about 0.1 ng to about 100 g per kg of, body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, the term "CpG motif" refers to a nucleotide sequence, which contains unmethylated cytosine-guanine dinucleotide linked by a phosphate bond.

As used herein, the term "CpG oligodeoxynucleotide" or "CpG ODN" refers to an oligodeoxynucleotide comprising at least one CpG motif and that binds TLR9.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Use of del(5q) Synthetic Lethal Pathway to Sensitize non-del(5q) Malignant Cells to Lenalidomide Myelodysplastic syndrome (MDS) is an aging-associated malignant bone marrow (BM) disorders with high risk for acute myeloid leukemia (AML) transformation. Lenalidomide (LEN) has emerged as the only targeted therapeutic approved for the treatment of a subtype of patients with chromosome 5q deletion (del5q). However, del(5q) patients only account for 5-10% of MDS cases while the majority of non-del(5q) patients are not responsive to LEN. LEN acts by inhibiting the activity of two haplodeficient phosphatases, PP2Acα and Cdc25C, encoded within the 5q region. They account for the disease's karyotype selective specificity. Small interfering RNA suppression of these genes' expression recapitulates del(5q) susceptibility to LEN with induction of apoptosis in non-del(5q) MDS cells. MDS progenitors overexpress TLR9, permitting development of an innovative disease-specific targeting approach using a single molecule containing: unmethylated CpG oligonucleotides (TLR9's ligands), siRNAs to Cdc25C-PP2A, and LEN, which renders non-del5q progenitors sensitive to clonal suppression by the drug.

Figure 2A:
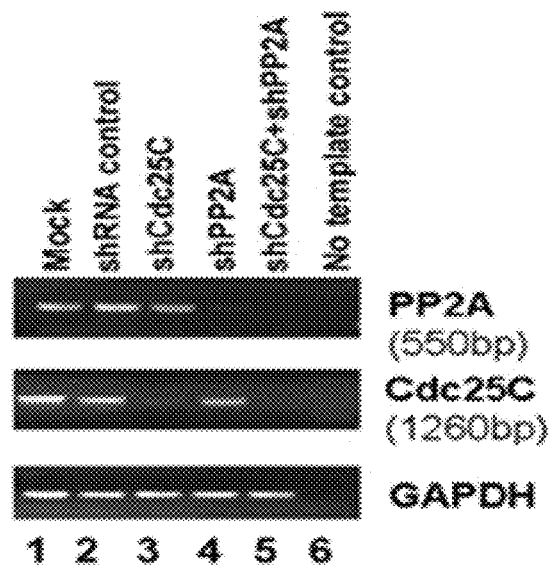
FIG. 2A-G shows that dual Cdc25C & PP2Acα Gene Knockdown increases apoptotic response to lenalidomide treated cells.
Figure 2B:
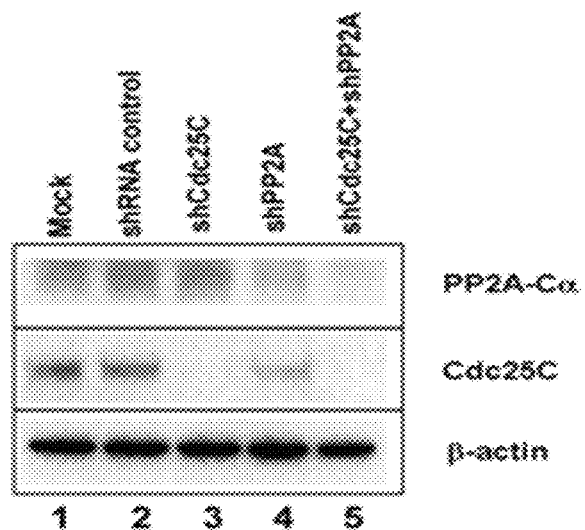
Figure 2C:
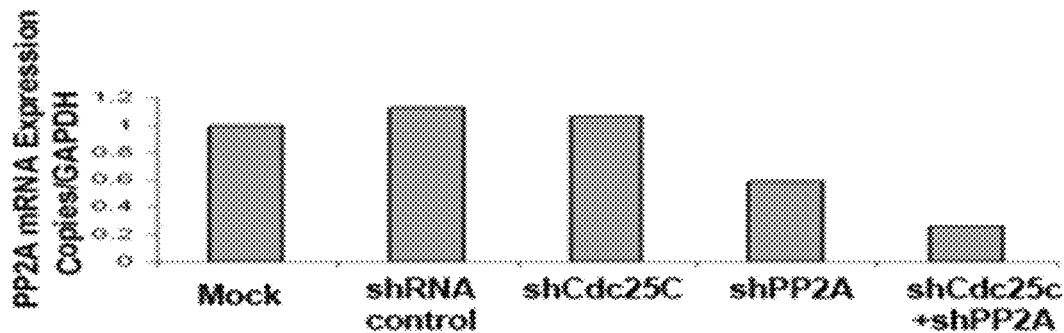
Figure 2D:
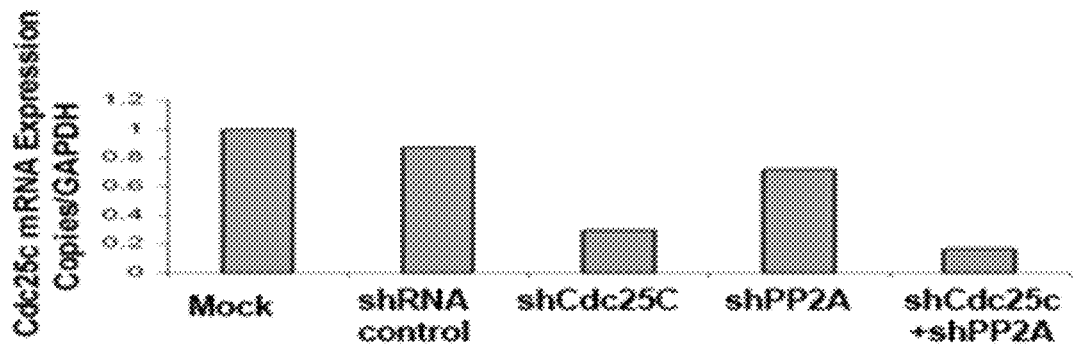
Figure 2E:
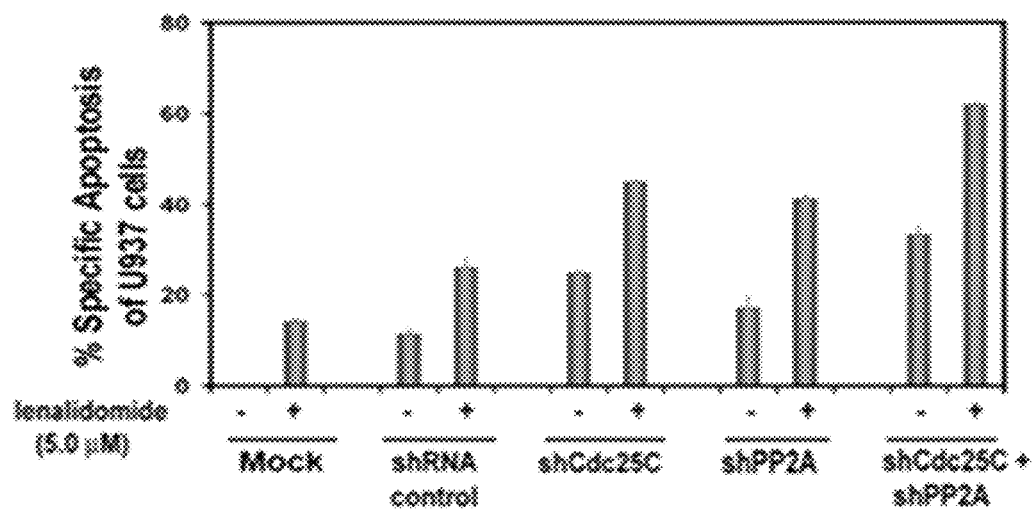
Figure 2F:
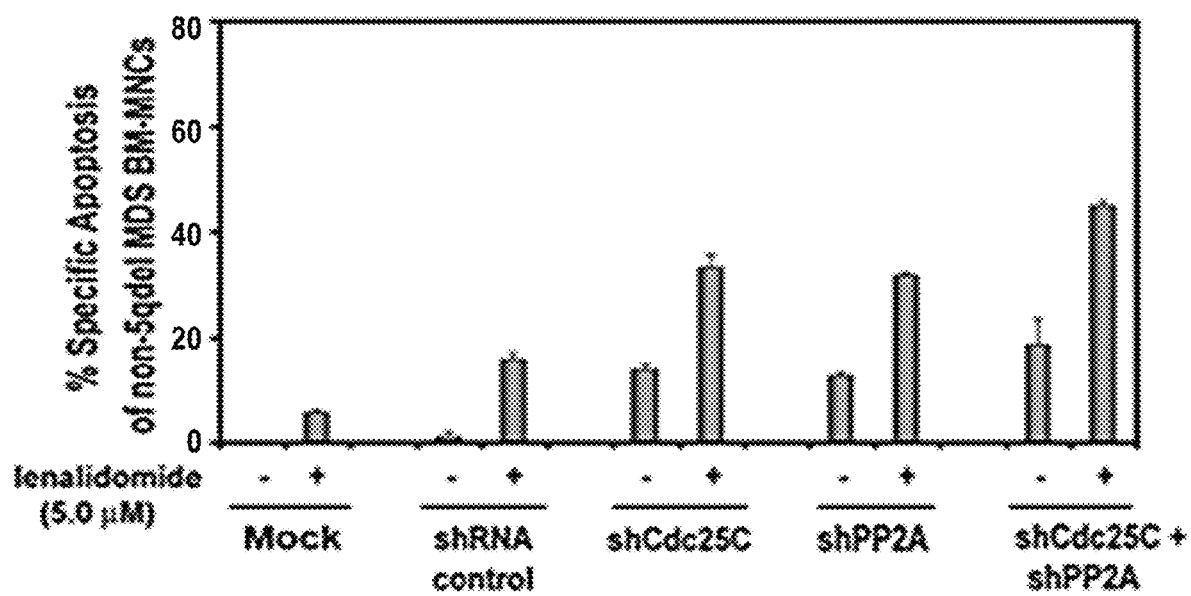
Figure 2G:
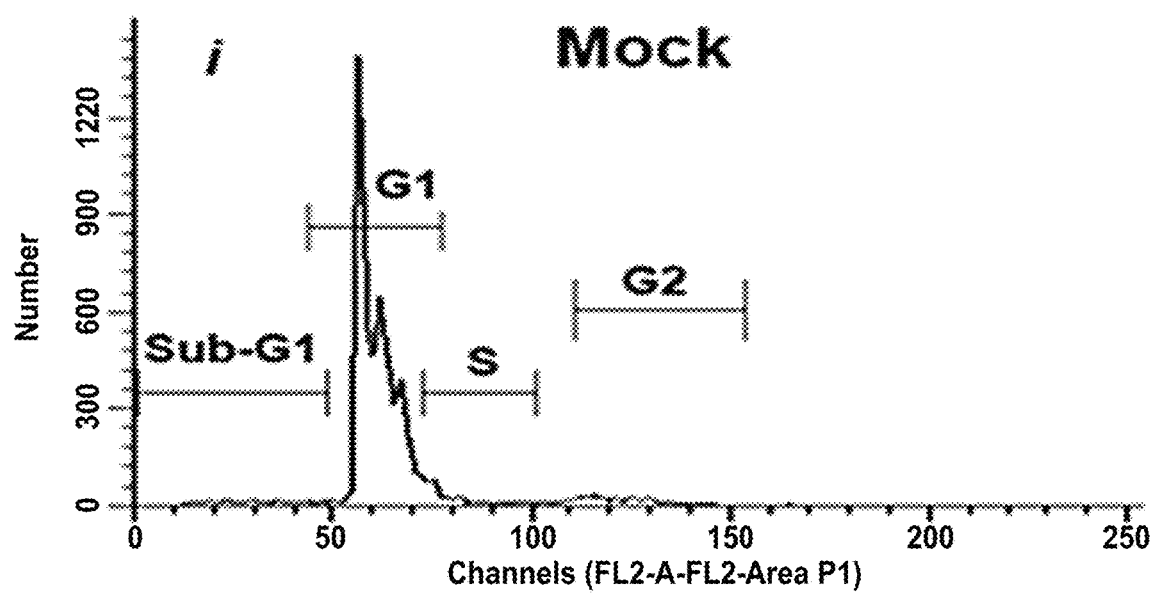
Figure 2G:
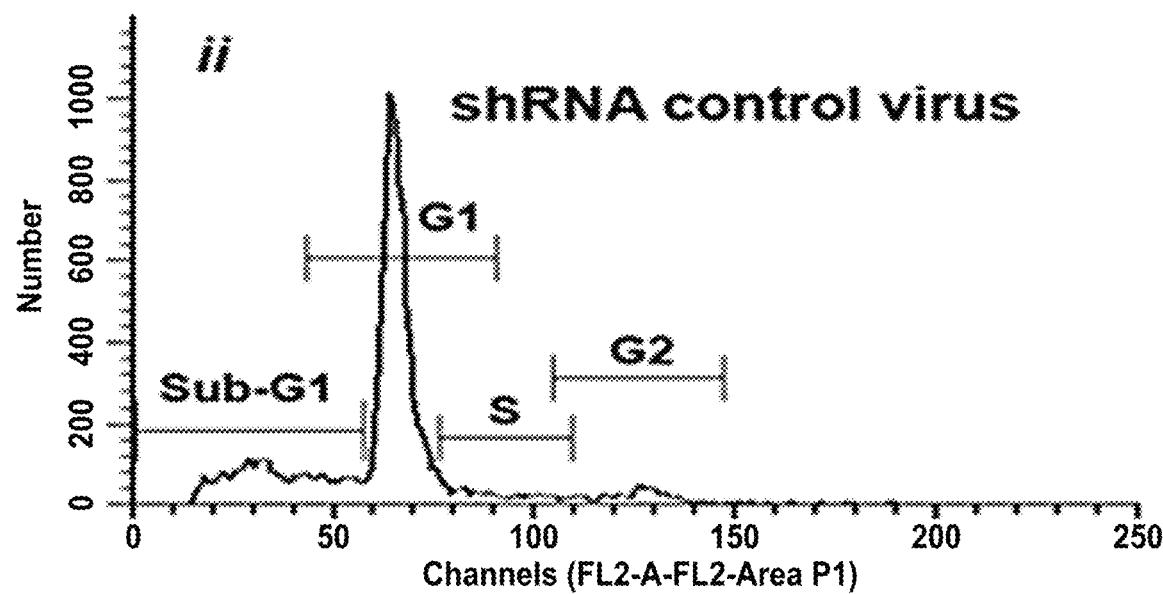
Figure 2G:
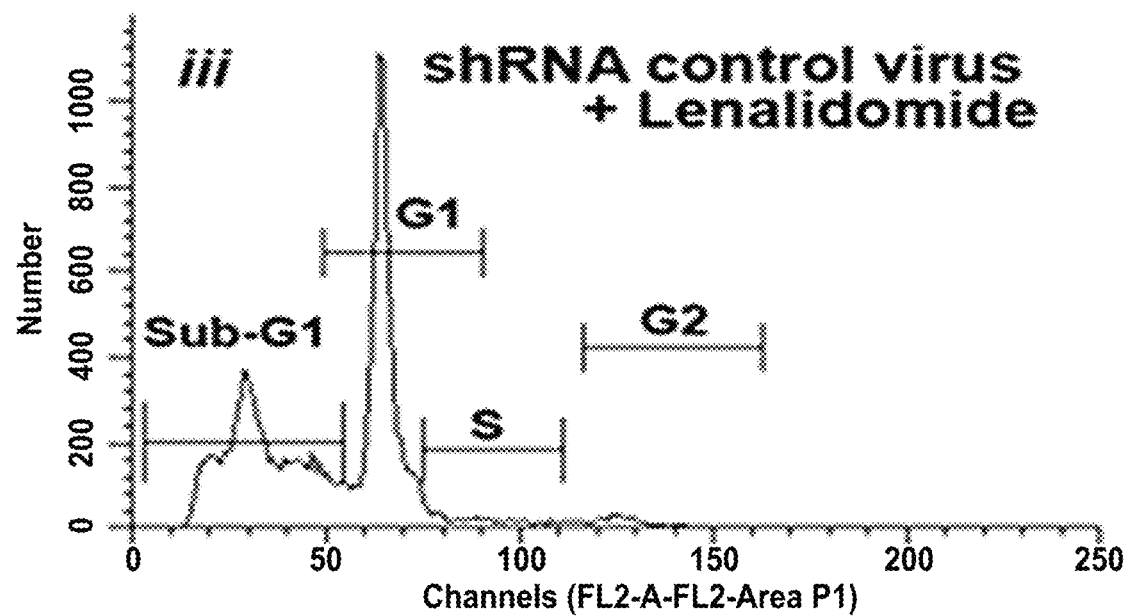
Figure 2G:
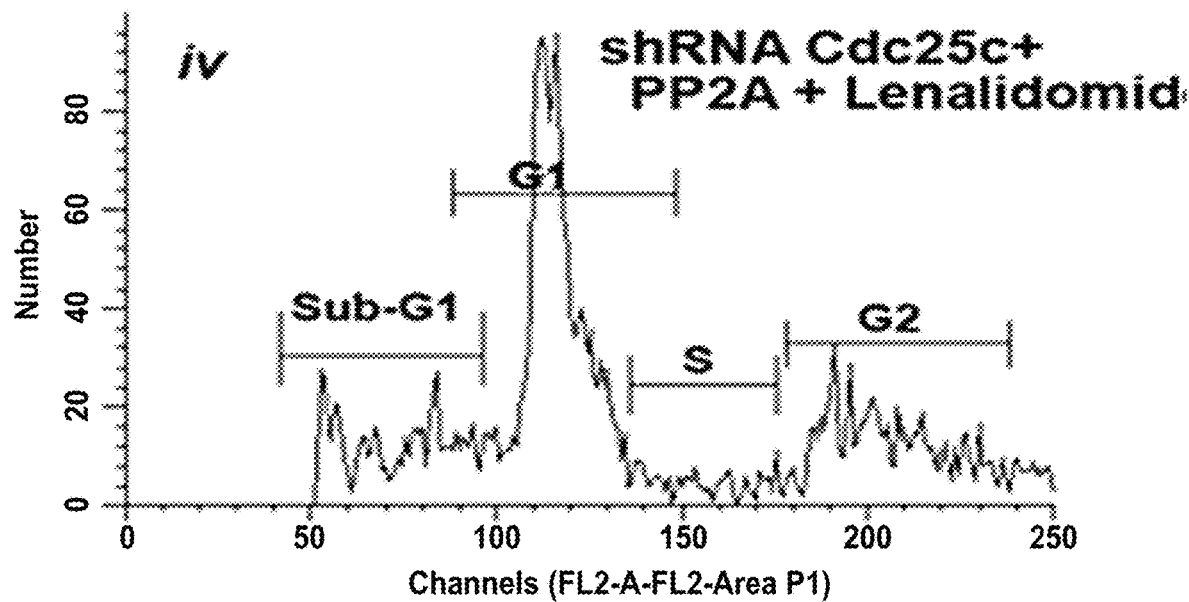

Dual Cdc25C & PP2Acα gene knockdown increases apoptotic response to lenalidomide treated cells. FIGS. 2A-2B show that dual shRNA Knockdown of Cdc25C and PP2Acα expression in lentivirus-infected U937 Cells. U937 cells were infected with mock (lane 1), lentiviral vectors encoding non-target shRNA control (lane 2), shCdc25C (lane 3), shPP2Acα (lane 4), shCdc25C and PP2Acα (lane 5) and negative for PCR (lane 6). After 48 hours of incubation, the cells were harvested for gene expression analysis using RT-PCR western blot analysis and Q-PCR analysis of the suppression effect of shRNA specific for PP2Acα and Cdc25C. Dual Cdc25C and PP2Acα gene knockdown increases apoptotic response to lenalidomide in U937 Cells and BM-MNC from non-(del)5q MDS patients. The U937 cells (FIG. 2C) or BM-MNC (FIG. 2D) were infected with lentiviral vectors containing various constructs as indicated for 48 hours and then treated with or without lenalidomide at the concentration of 5 μM for additional 48 hours before analyzed for apoptosis. The difference between Cdc25C and PP2Acα double-knockdown plus lenalidomide treatment and shRNA control plus lenalidomide was statistical significant (p<0.001) in five MDS patients with a normal karyotype. FIG. 2G shows cell cycle analysis of BM-MNC from MDS patients with a normal karyotype after Cdc25C/PP2Acα double-knockdown plus lenalidomide treatment. A representative result is shown from one patient. A total of five different MDS patients were tested.

Figure 3A:
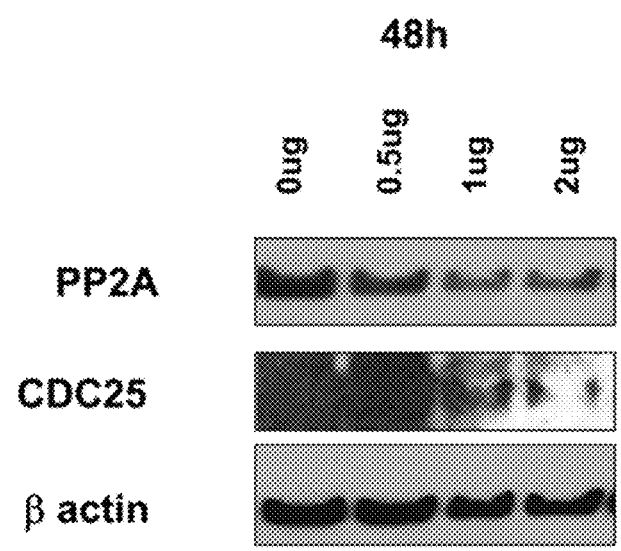
FIG. 3A-D shows the effect of linker conjugated siPP2A-Cdc25C and LEN on nondel5q cells in a dose dependent manner.
Figure 3B:
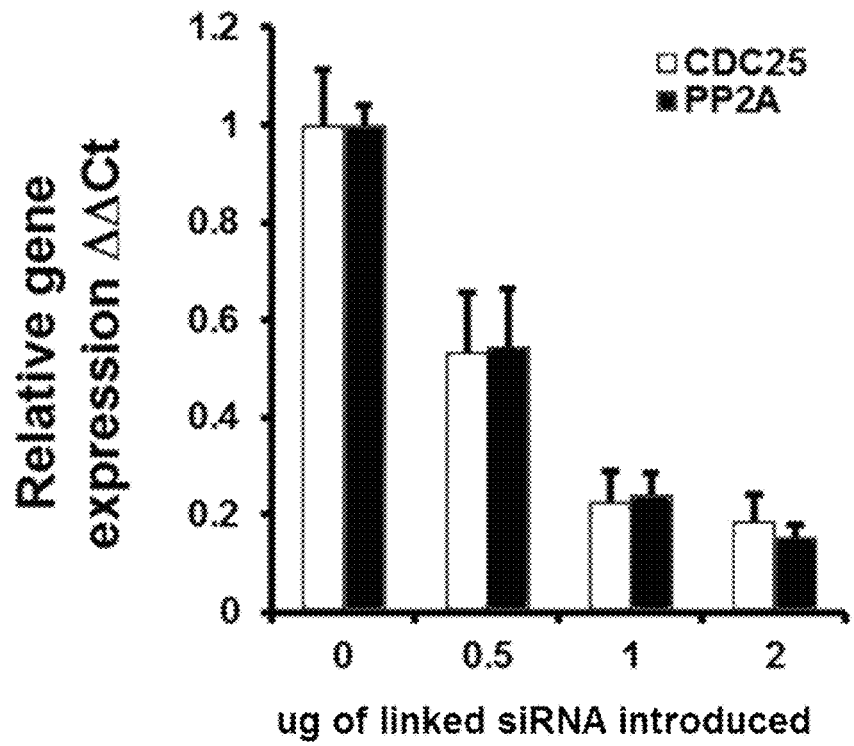
Figure 3C:
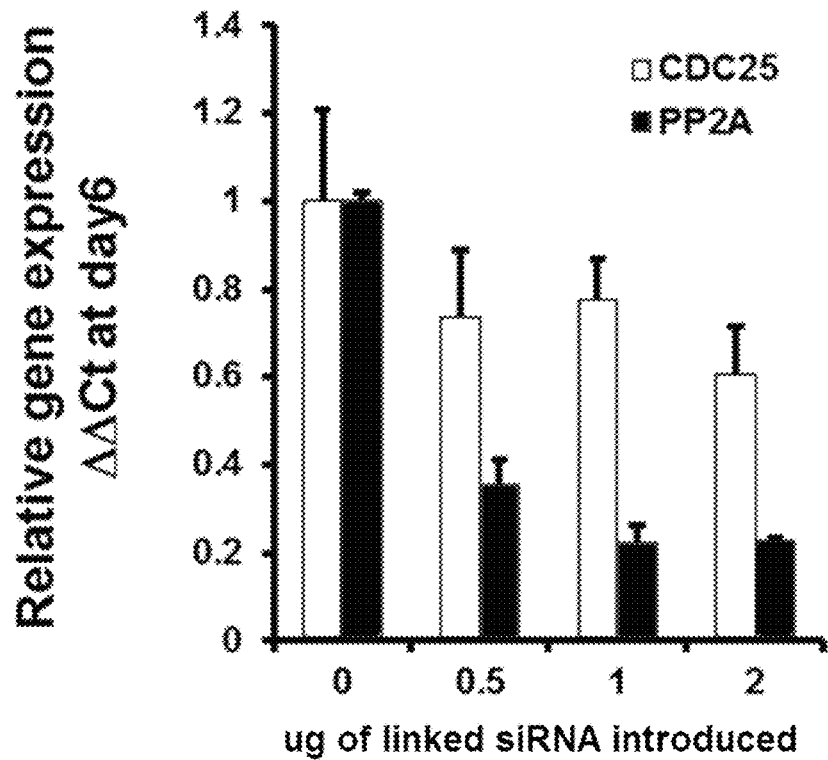
Figure 3D:
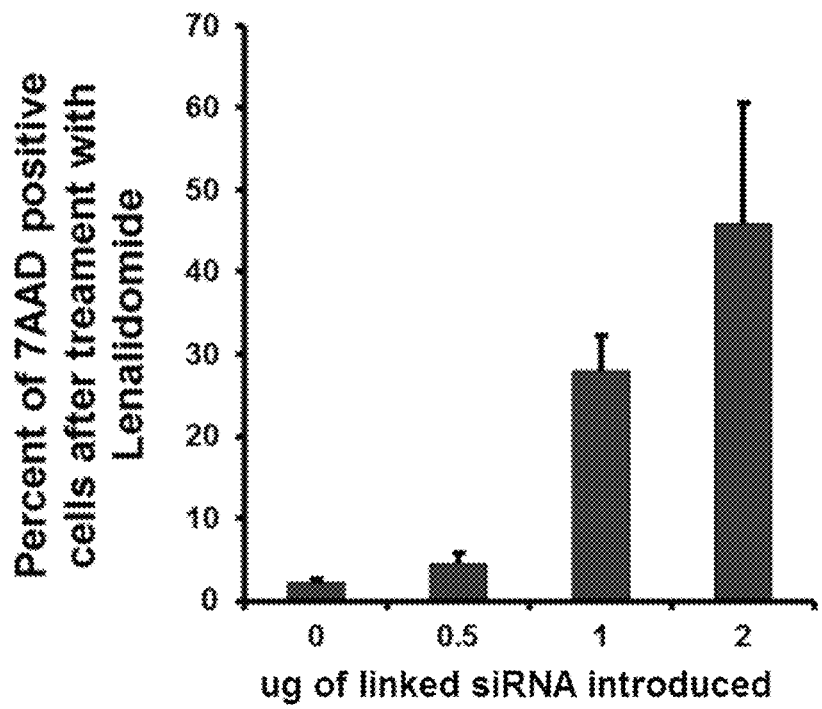

FIG. 3 shows the effect of linker conjugated siPP2A-Cdc25C and LEN on nondel5q cells in a dose dependent manner. siPP2A and Cdc25c linked by C3 linker were transfected into U937 cells for 48 hours and PP2Aca and Cdc25C expression were measured either by Western blot analysis with anti-PP2Aca and Cdc25C antibody (FIG. 2A) or by Q-PCR (FIG. 3B). FIG. 3C shows gene silencing by linked siRNA is sustained at day 6 by Q-PCR after transfection. FIG. 3D shows linked siPP2A and Cdc25c coupled with LEN transfected into U937 cells & apoptosis measured at 72 hours.

Figure 4A:
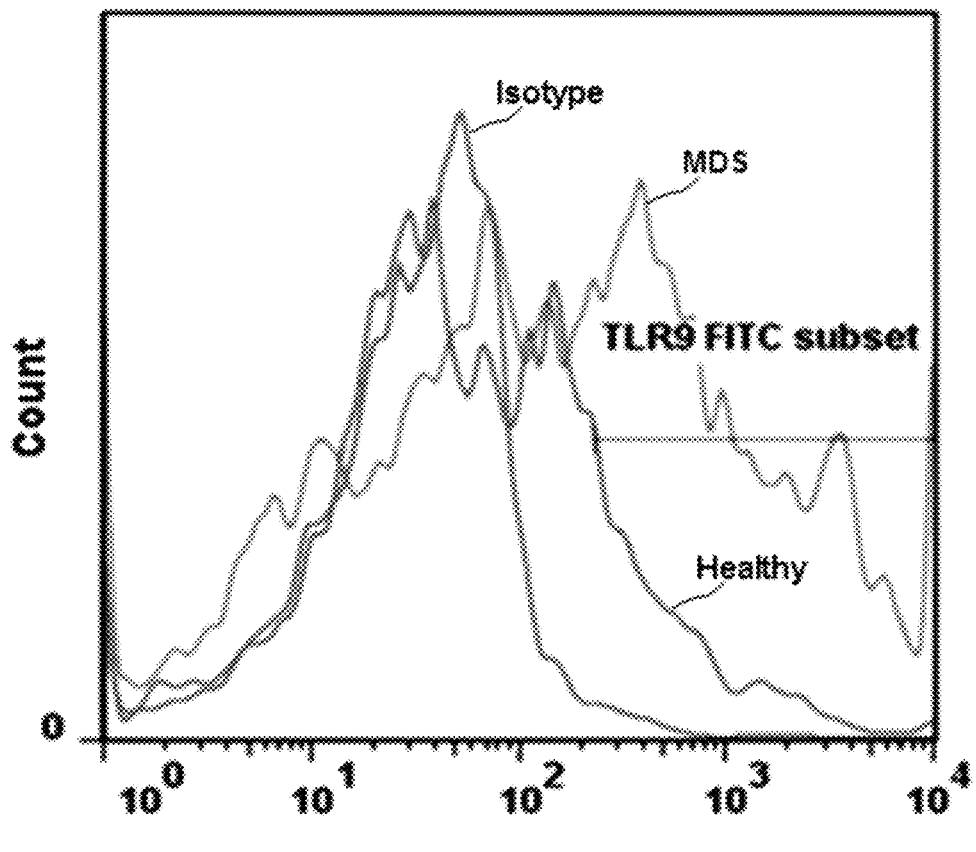
FIG. 4A-C shows increased TLR9 expression in primary BM specimens from lower risk non-del5q MDS patients.
Figure 4B:
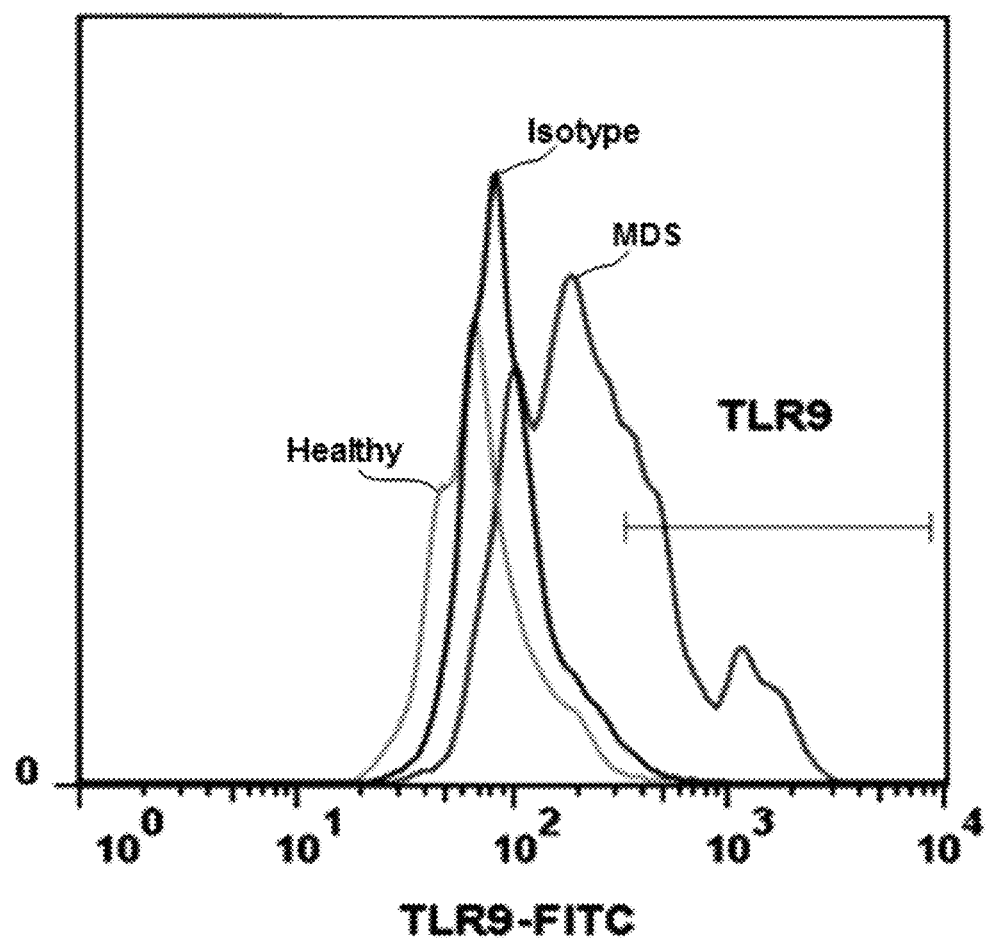
Figure 4C:
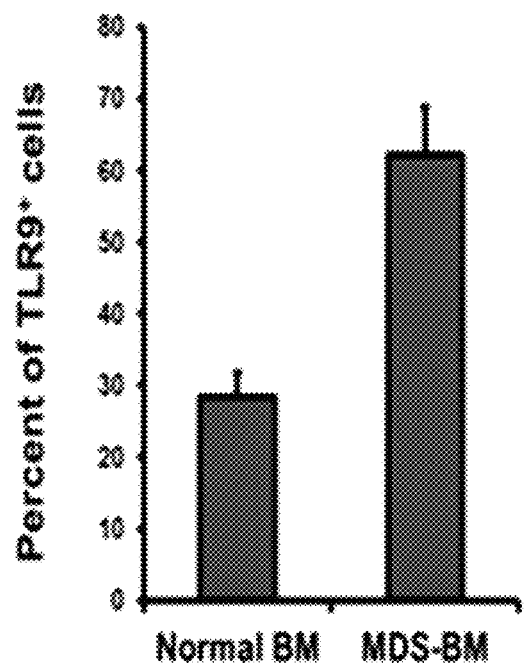

FIG. 4 shows increased TLR9 expression in primary BM specimens from lower risk non-del5q MDS patients. FIG. 4A shows flow cytometric analysis of TLR9 surface expression on BM-MNCs from MDS patients or age-matched healthy donors with anti-TLR9. FIG. 4B shows flow cytometric analysis of TLR9 surface expression on CD34+ CD90+ double positive HSCs from MDS patients or age-matched healthy donors with anti-TLR9. One representative experiment is shown and a total of 6 patients and 4 controls were examined and summarized in FIG. 4C.

Figure 5A:
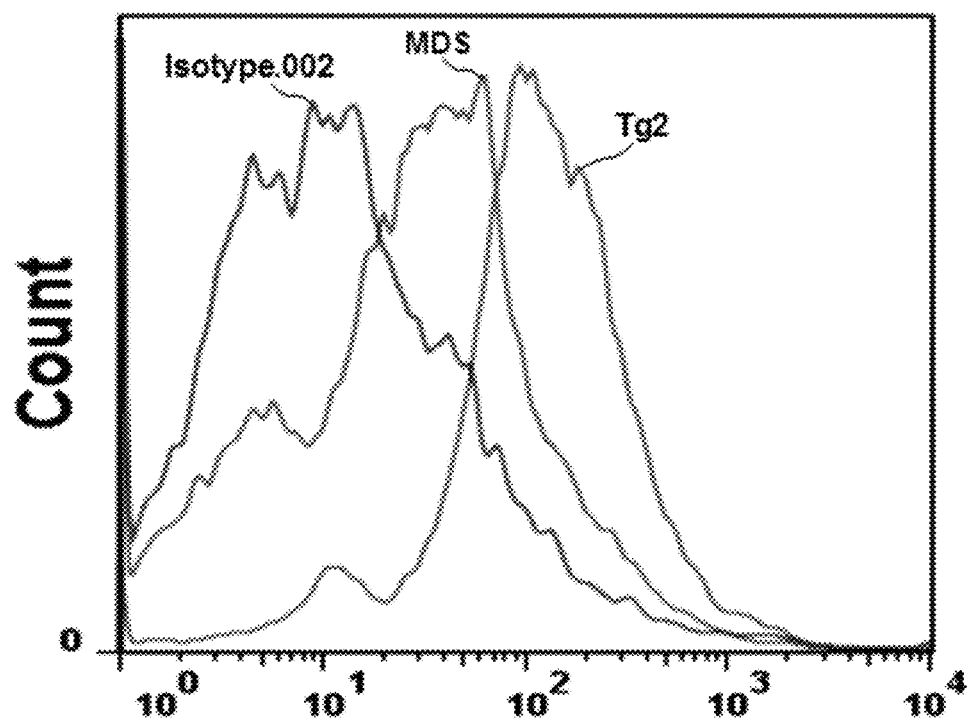
FIG. 5A-B is a graph showing increased TLR-9 surface expression in S100A9Tg mice compared with wild-type mice.
Figure 5B:
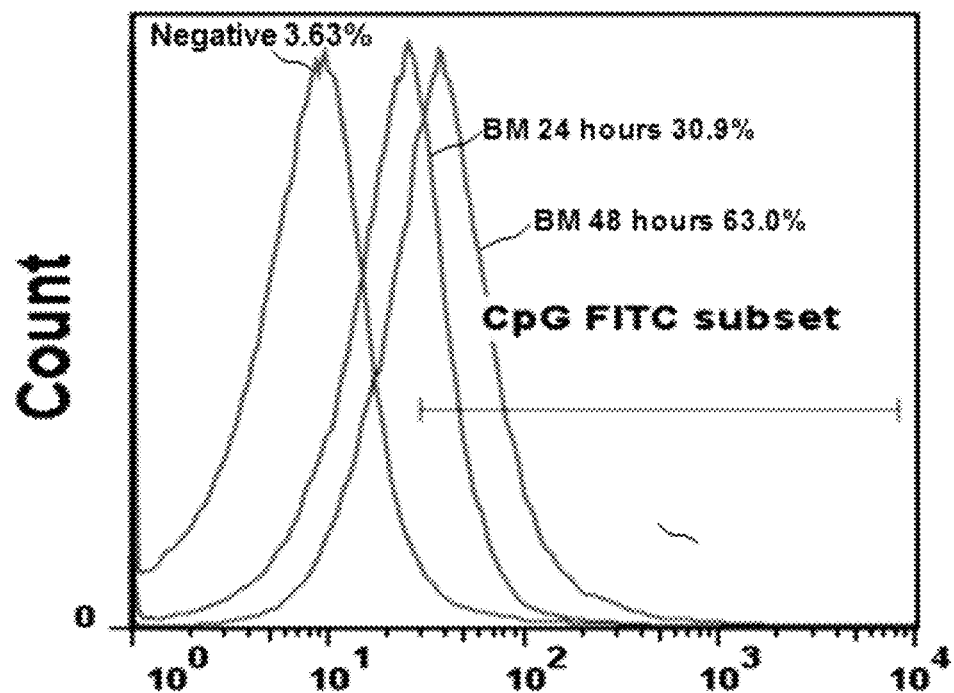

FIG. 5A shows that there is an increased TLR-9 surface expression in S100A9Tg mice compared with wild-type mice. FIG. 5B shows that there is increased intracellular FITC positive bone marrow cells examined by intracellular flow cytometric analysis after injection of FITC labeled CpG conjugates (25 μg/100 μl/per mouse) at 24 or 48 hours by tail injection.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A molecule comprising
   an oligonucleotide inhibitor of Cdc25C that directly inhibits gene expression of Cdc25C, an oligonucleotide inhibitor of PP2Acα that directly inhibits gene expression of PP2Acα, or a combination thereof;
   a toll like receptor-9 (TLR9) targeting ligand; and
   lenalidomide.

2. The molecule of claim 1, comprising the oligonucleotide inhibitor of Cdc25C coupled to the oligonucleotide inhibitor of PP2Acα by a bivalent linker.

3. The molecule of claim 1, wherein the TLR9 targeting ligand is coupled to the oligonucleotide inhibitor of Cdc25C or the oligonucleotide inhibitor of PP2Acα by a bivalent linker.

4. The molecule of claim 1, wherein the lenalidomide is coupled to the oligonucleotide inhibitor of Cdc25C or the oligonucleotide inhibitor of PP2Acα by a bivalent linker.

5. The molecule of claim 1, wherein the molecule is defined by the formula:

TTL--IC--IP--LEN, or

TTL--IP--IC--LEN, wherein "TTL" represents a TLR9 targeting ligand,
   wherein "IC" represents an siRNA inhibitor of Cdc25C,
   wherein "IP" represents an-siRNA inhibitor of PP2Acα,
   wherein "LEN" represents an lenalidomide, and
   wherein "--" represents a bivalent linker.

6. The molecule of claim 1, wherein the TLR9 targeting ligand is an unmethylated CpG oligodeoxynucleotide.

7. The molecule of claim 1, wherein the oligonucleotide inhibitor of Cdc25C is an siRNA.

8. The molecule of claim 1, wherein the oligonucleotide inhibitor of Cdc25C comprises the nucleic acid sequence SEQ ID NO:1, or a nucleic acid sequence having at least 80% sequence identity to SEQ ID NO:1.

9. The molecule of claim 1, wherein the oligonucleotide inhibitor of PP2Acα is an siRNA.

10. The molecule of claim 1, wherein the oligonucleotide inhibitor of PP2Acα comprises the nucleic acid sequence SEQ ID NO:2, or a nucleic acid sequence having at least 80% sequence identity to SEQ ID NO:2.

11. A pharmaceutical composition comprising the molecule of claim 1 in a pharmaceutically acceptable carrier.

12. A method for treating non-del(5q) myelodysplastic syndrome (MDS) in a subject, comprising administering to the subject a therapeutically effective amount of the pharmaceutical composition of claim 11.

* * * * *

```
                        SEQUENCE LISTING

<160> NUMBER OF SEQ ID NOS: 2

<210> SEQ ID NO 1
    <211> LENGTH: 21
    <212> TYPE: RNA
    <213> ORGANISM: Artificial Sequence
    <220> FEATURE:
    <223> OTHER INFORMATION: Synthetic Construct

<400> SEQUENCE: 1
gaagagaaua aucaucgugu u                                          21

<210> SEQ ID NO 2
    <211> LENGTH: 21
    <212> TYPE: RNA
    <213> ORGANISM: Artificial Sequence
    <220> FEATURE:
    <223> OTHER INFORMATION: Synthetic Construct

<400> SEQUENCE: 2
uggaacuuga cgauacucua a                                          21
```